(12) United States Patent
Lucke et al.

(10) Patent No.: US 7,364,563 B2
(45) Date of Patent: Apr. 29, 2008

(54) CONTINUOUS VOLUME DETECTION FOR A FLEXIBLE VENOUS RESERVOIR IN A CARDIOPULMONARY BYPASS CIRCUIT

(75) Inventors: Lori E. Lucke, Eagan, MN (US); Matthew J. Cunningham, Brooklyn Park, MN (US); Richard A. Nazarian, Maple Grove, MN (US)

(73) Assignee: Minnetronix, Inc., Minneapolis, MN (US)

(*) Notice: Subject to any disclaimer, the term of this patent is extended or adjusted under 35 U.S.C. 154(b) by 274 days.

(21) Appl. No.: 10/957,528

(22) Filed: Oct. 1, 2004

(65) Prior Publication Data

US 2005/0119600 A1 Jun. 2, 2005

Related U.S. Application Data

(60) Provisional application No. 60/507,993, filed on Oct. 2, 2003.

(51) Int. Cl.
*A61M 37/00* (2006.01)
*A61M 1/00* (2006.01)
*G01F 19/00* (2006.01)
*G01F 17/00* (2006.01)
*G01N 11/00* (2006.01)

(52) U.S. Cl. .................. 604/6.15; 422/44; 422/45; 73/1.73; 73/53.04; 73/149; 702/50; 702/55

(58) Field of Classification Search .......... 422/44–48; 604/403–416, 4.01–6.16; 436/16; 702/33, 702/50, 55; 73/1.01, 1.16, 1.73, 53.04, 61.64, 73/61.73, 149
See application file for complete search history.

(56) References Cited

U.S. PATENT DOCUMENTS

| | | | | |
|---|---|---|---|---|
| 5,964,724 A | * | 10/1999 | Rivera et al. | 604/5.04 |
| 6,113,554 A | * | 9/2000 | Gilcher et al. | 600/573 |
| 6,256,643 B1 | * | 7/2001 | Cork et al. | 707/205 |
| 6,413,233 B1 | * | 7/2002 | Sites et al. | 604/6.13 |
| 6,537,495 B1 | * | 3/2003 | Cambron et al. | 422/45 |
| 6,548,017 B2 | * | 4/2003 | Krivitski et al. | 422/44 |
| 6,691,040 B2 | * | 2/2004 | Bosetto et al. | 702/19 |
| 6,730,054 B2 | * | 5/2004 | Pierce et al. | 604/6.01 |
| 6,735,532 B2 | * | 5/2004 | Freed et al. | 702/50 |
| 6,858,146 B1 | * | 2/2005 | Myers et al. | 210/644 |
| 7,072,769 B2 | * | 7/2006 | Fletcher-Haynes et al. | 702/21 |

* cited by examiner

*Primary Examiner*—Tatyana Zalukaeva
*Assistant Examiner*—Phil Wiest
(74) *Attorney, Agent, or Firm*—Shumaker & Sieffert, P.A.

(57) ABSTRACT

A continuous volume detection system for a flexible venous reservoir in a cardiopulmonary bypass circuit is described. The volume detection system is based on a pressure measurement that is manipulated via application of fluid mechanics. Next-generation cardiopulmonary bypass system controllers may use this data to control the volume contained in the flexible venous reservoir.

15 Claims, 13 Drawing Sheets

CONTINUOUS VOLUME DETECTION FOR A FLEXIBLE VENOUS RESERVOIR IN A CARDIOPULMONARY BYPASS CIRCUIT

CROSS-REFERENCE TO RELATED APPLICATIONS

This Application claims the benefit of U.S. Provisional Application No. 60/507,993, filed Oct. 2, 2003, the entire content of which is incorporated herein by reference.

TECHNICAL FIELD

The invention relates to medical systems.

BACKGROUND

During cardiopulmonary bypass surgery, blood must be oxygenated and circulated artificially outside of the body. For external circulation to be successful, it is critical to provide a method for passive venous drainage and to prevent air bubbles from entering the bypass circuit. If an air bubble finds its way to the human brain, consequences include brain damage and death. The venous reservoir component of the cardiopulmonary bypass circuit provides passive drainage, but is especially susceptible to air bubble introduction. Two types of reservoir exist, the flexible reservoir and the hard-sided reservoir. A primed flexible reservoir is much less likely to introduce bubbles into the circuit than its counterpart, due to its ability to conform its shape to accommodate the volume of blood in the reservoir.

Currently, level detection is available for the hard-sided reservoir in the form of acoustic sensors that attach to the container. These sensors are capable of determining whether or not fluid has reached a certain level. Due to its nature, this detection mechanism is not capable of providing continuous volume data.

Level detectors have taken on many forms throughout their evolution. Capacitance, weight, and light-based systems are a few of the level detection methods that experienced limited success. However, these systems were plagued with issues, as in the weight-based system, where "the tragic defect in this device is that the device cannot differentiate between blood in the arterial reservoir and someone leaning on the weight arm. There have been reports of someone pushing down on the arm, the arterial pump head going to maximum RPM, and air being pumped into the patient."

In terms of benefits, electronic level sensing relieves the perfusionist (the person in charge of the bypass circuit) of the extraneous duty of monitoring the venous reservoir. By eliminating a task for the perfusionist, this system will also reduce the likelihood of human error.

SUMMARY

In general, the invention is directed to techniques for automatically determining volume in a flexible venous reservoir by pressure measurements. The pressure-volume characteristics of a static reservoir is analyzed, and is used as a basis for evaluation of a dynamic environment in which fluid is flowing into and out of the venous reservoir. Bernoulli's principle for an ideal fluid is applied to predict the pressure response for this situation. The fluid flow of the system is measured, and is applied to accurately predict the pressure drop introduced by fluid flow. The pressure can then be reconstructed and considered in a static sense.

The techniques described herein include, characterization of a flexible reservoir pressure response, system integration to prove or dismiss feasibility, signal processing to remove pressure noise, and pressure drop due to fluid flow. These and other techniques are described herein with respect to automatically determining volume in a flexible venous reservoir by pressure measurements.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
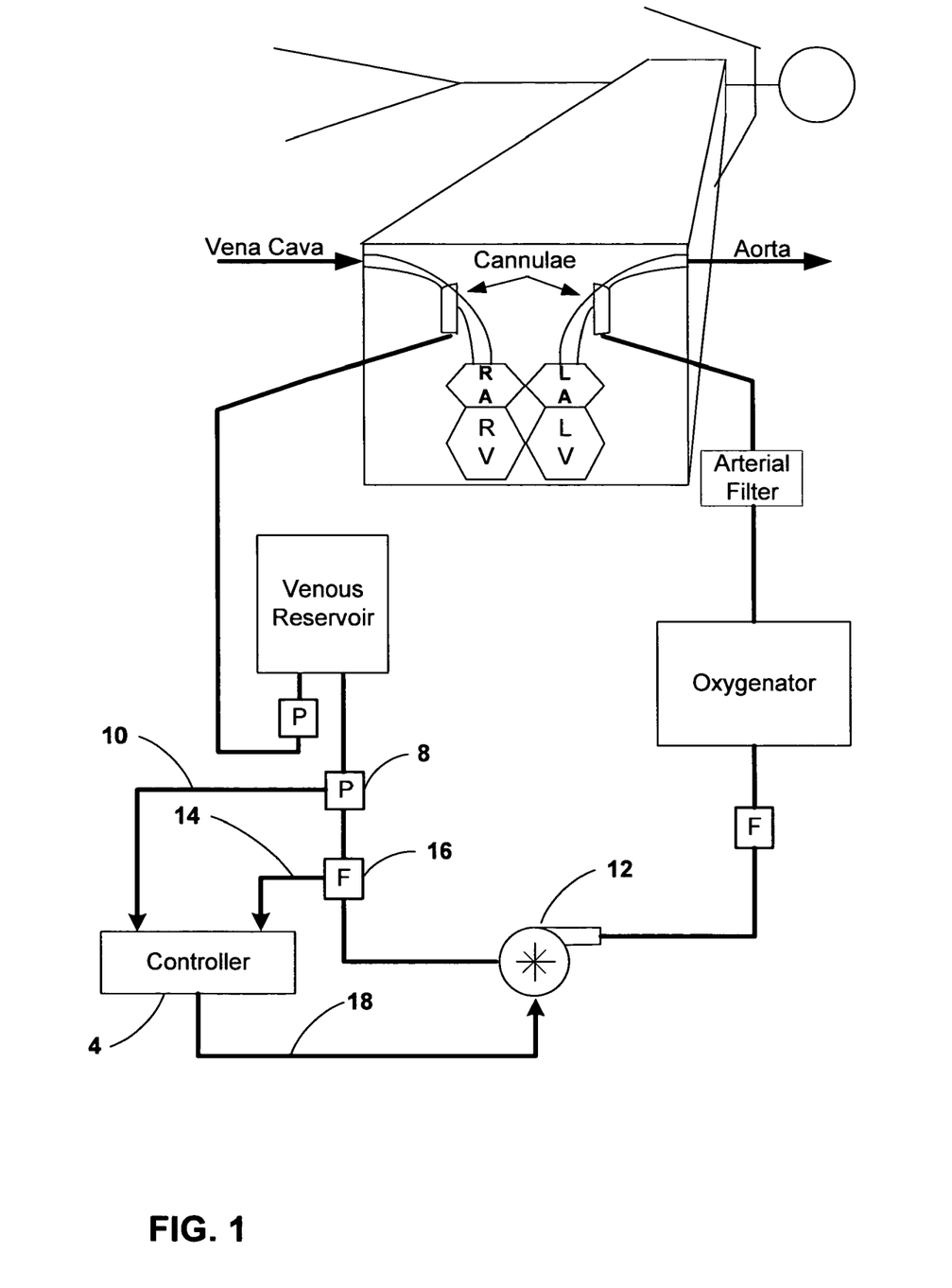
FIG. 1 is a block diagram illustrating an example embodiment of a cardiopulmonary bypass circuit in which a controller applies the pressure-based level sensing techniques described herein.

FIG. 1 is a block diagram illustrating an example embodiment of a cardiopulmonary bypass circuit in which a controller 4 applies the pressure-based level sensing techniques described herein. As illustrated, the exemplary bypass circuit includes the following elements: a person's elevated circulatory system, two cannulae that route blood into and out of the person's circulatory system, a venous reservoir for blood storage, a pump that provides blood flow, an oxygenator to oxygenate the blood, and an arterial filter to remove blood contaminants. It should be noted that this is a simplified representation, and that there are many variations on the circuit.

In the illustrated embodiment, pressure sensor 8 is connected near an outlet of the venous reservoir, and generates a pressure signal 10 representative of the sensed pressure. In one embodiment, pressure sensor 8 is a diaphragm pressure sensor coupled to the outlet tubing via a tap. Pressure sensor 8 may generate signal 10 an analog voltage sensor is connected near the bottom of the venous reservoir. The output voltage of pressure sensor 8 may be directly proportional to the pressure detected by the sensor.

Flow sensor 16 generates signal 14 representative of a fluid velocity of the fluid exiting the venous reservoir. In the exemplary embodiment, flow sensor 16 is illustrated as positioned downstream from pressure sensor 8 for exemplary purposes. In other embodiments flow sensor 16 may be positioned in other areas of the system.

As described in detail herein, controller 4 receives pressure signal 10 and flow signal 14, and calculates a current volume of blood within the venous reservoir. Based on the calculated volume, controller 4 may output control signal 18 to provide automatic regulation of the pump 12, thereby dynamically adjusting the flow of blood through the cardiopulmonary bypass circuit. In addition, controller 4 may present an indicator of the current volume of blood contained within the venous reservoir. Controller 4 may, for example, present a graphical representation of soft or hard container, and a visual indicator of the current blood level within the container. As other examples, controller 4 may output an audible warning if the volume of blood within the venous reservoir drops to a programmably defined level.

In one embodiment, pump 12 may be a roller pump having an output signal that represents the speed of the pump. Controller 4 may make use of this speed signal to calculate the blood flow velocity.

Figure 2:
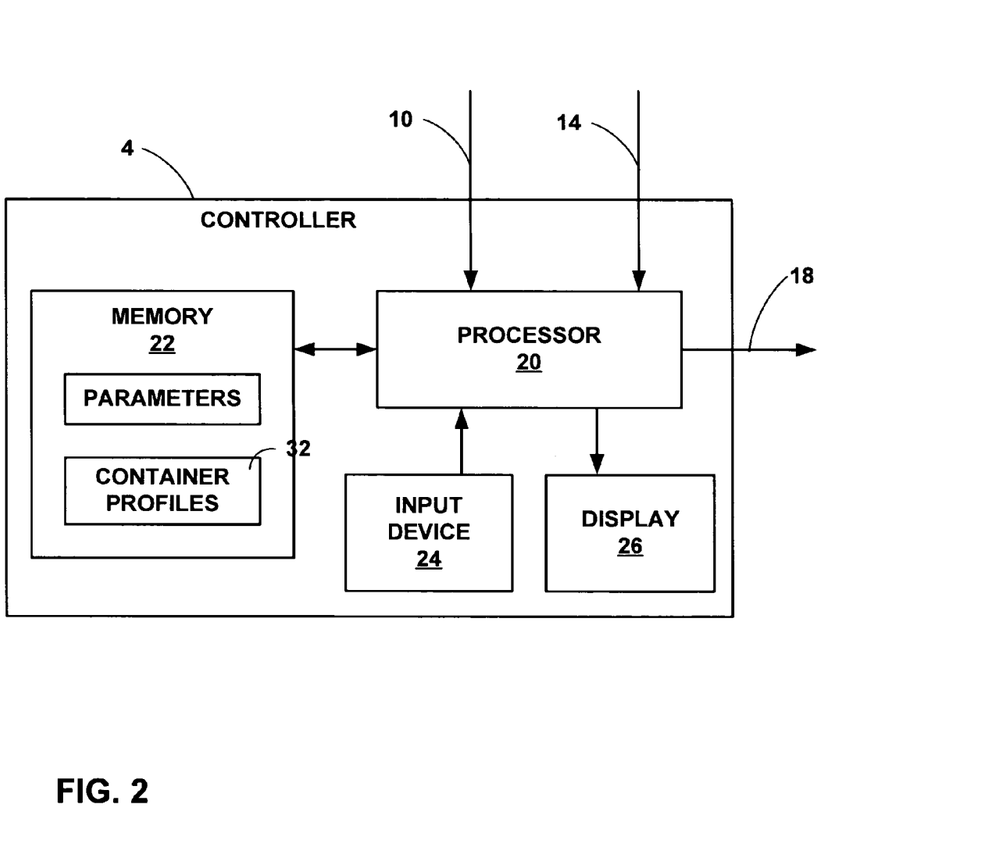
FIG. 2 is a block diagram illustrating an exemplary embodiment of the controller of FIG. 1.

FIG. 2 is a block diagram illustrating an exemplary embodiment of controller 4. In the illustrated embodiment, controller 4 includes a processor 20, a memory 22, an input device 24 and a display 26.

Memory 22 stores a set of container profiles 32, in which each profile as associated with a particular type of container for use as the venous reservoir. For example, a container profile may be created for each type of hard container and/or soft container that may be used within the system. Each profile characterizes the respective container in a manner that allows controller 4 to accurately calculate the volume of blood with the venous reservoir. Each profile may, for example, store a set of coefficients for application by controller 4 to a polynomial that uniquely maps pressure to the volume for the respective location. The polynomial mapping may comprise, for example, a $5^{th}$ order polynomial.

Memory 22 may also store other parameters that may be used during the volume calculation. Example parameters include a distance from which pressure sensor 8 is located from the outlet of the venous reservoir, and patient specific parameters, such as hematocrit characteristics of the patient that may influence blood viscosity.

Controller 4 receives programmable input, e.g., a current type of hard or soft container, position of pressure sensor 8, patient-specific attributes. Based on the programmable input, controller 4 selects one of the profiles 32, and calculates a current volume of blood within the venous reservoir as a function of pressure signal 10 and flow signal 14.

In another embodiment, memory 22 may comprise a look-up table for which volume levels of the venous reservoir have been pre-calculated as a function of bag type, sensed pressure, sensed flow velocity, and other parameters.

Controller 4 presents on display 26 an indicator of the current volume of blood contained within the venous reservoir. Controller 4 may, for example, present a graphical representation of soft or hard container, and a visual indicator of the current blood level within the container. As other examples, controller 4 may output an audible warning if the volume of blood within the venous reservoir drops to a programmably defined level.

Controller 4 may include a secondary output port, e.g., a network connection, to communicate the computed volume to another medical device or system.

Figure 3:
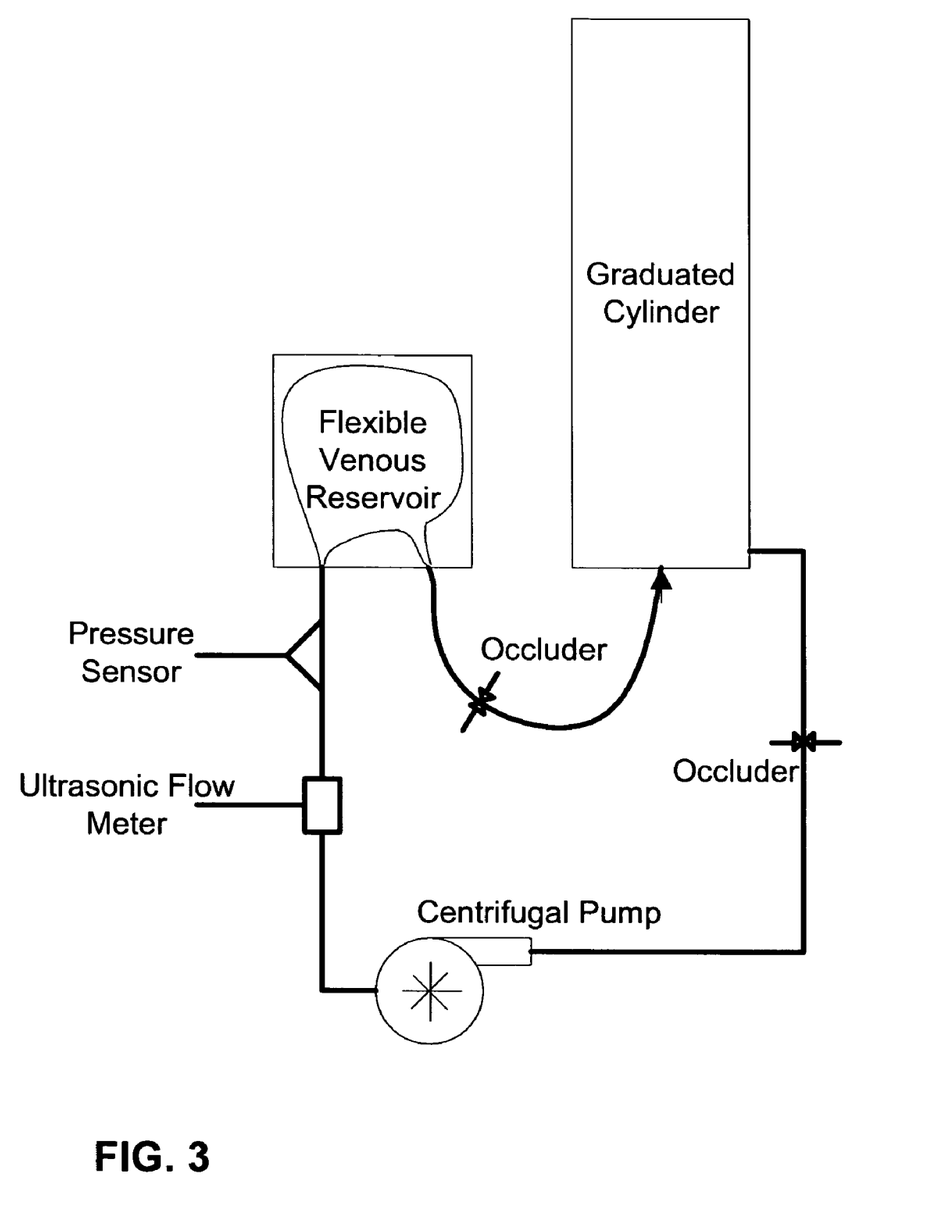
FIG. 3 displays an exemplary lab configuration used for evaluating the techniques described herein.

FIG. 3 displays an exemplary test lab configuration used for evaluating the techniques described herein. The flexible venous reservoir used was a 1500 ml Sarns Flexible Venous Reservoir, which is hung from an adjustable vertical support. A clear plastic PVC pipe was calibrated and used as a 5 L graduated cylinder. Tube occlusion elements were used to restrict fluid flow into and out of each member.

Data analysis was performed using both Microsoft Excel 97 and Microcal Origin 5.0. Excel was used to store and manipulate data, calculate x-error compensation, and for quick trend analysis. Origin was used for its advanced curve fitting (3rd and 5th order polynomials) with error weighting and three-dimensional graphing capabilities.

In order to resolve an accurate volume measurement for a particular pressure value, it was necessary to characterize the pressure-volume relationship in the 1500 ml Sarns Flexible Venous Reservoir. Also, in the clinical setting, it would be ideal to have a systematic approach to volume detection system setup. To provide a systematic approach to setup, a consistent way of zeroing the pressure sensor must be established, and is explored in this section.

Characterization of the reservoir was accomplished by gravity filling the reservoir from the graduated cylinder. The occluder, a passive device that attaches to the outside of the tubing in order to restrict flow, was carefully released to fill the reservoir with a precise volume of water. The water was allowed time to stabilize, and a pressure measurement was taken a few inches from the reservoir outlet. To ensure repeatability, data was taken three times for each of three different reservoirs and compiled.

After reviewing the raw data, it was determined that the one method of zeroing the pressure would be to concentrate on the area of minimal pressure change, which occurs throughout the middle of the reservoir's volume. By offsetting the pressure such that the half-volume point corresponds to zero pressure, minimal error is introduced if the volume is not exactly at the half-volume point. Also, measurement accuracy would not suffer potential pressure offsets introduced at the volume extremes.

Figure 4:
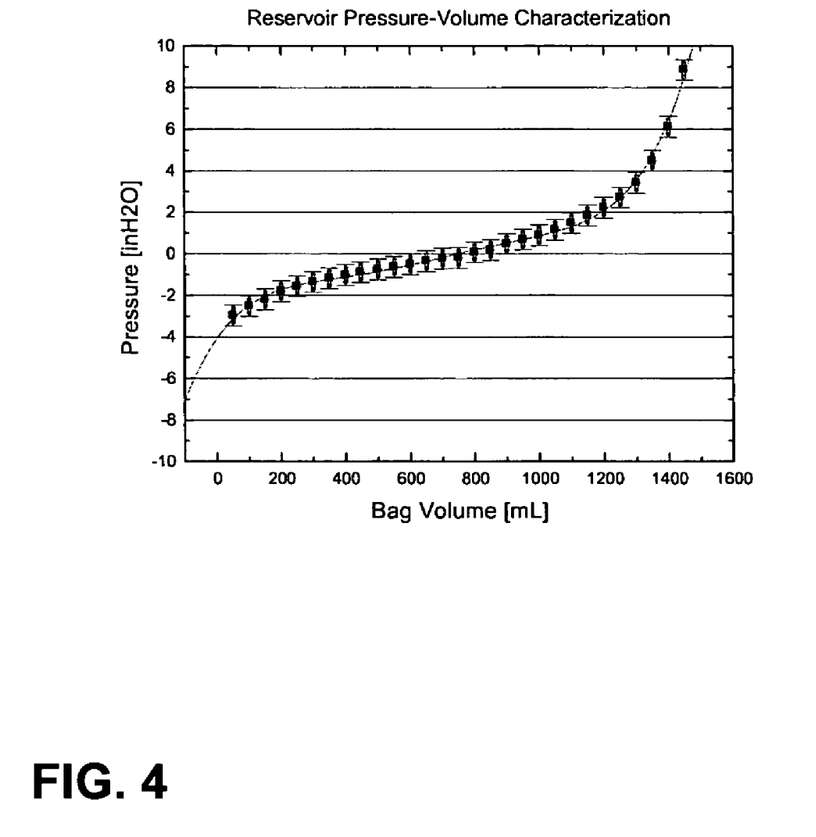
FIGS. 4-11 are graphs.

For curve fitting purposes, data was shifted on the x-axis such that the half-volume point was also centered at zero. This removes the offset in each of the x parameters in a polynomial fit of the data. FIG. 4 displays the pressure-volume response seen in characterization of the reservoir.

Techniques were developed to remove any pressure noise created by the centrifugal pump that was used to introduce fluid flow to the system. Because the changes in our target signal (i.e. the reservoir's volume-generated pressure) occur very slowly, only low frequency pressure signals were needed. The pressure signal was sampled by the hardware/software at 100 Hz. An analog low-pass filter with a 30 Hz cutoff and 6 dB/octave of attenuation was used on the front end to prevent aliasing. The remainder of the signal processing was done in software.

Because the reservoir is to be maintained throughout a bypass surgery, one can conclude that the volume in the reservoir is not allowed to change rapidly. For this reason, a digital low-pass Butterworth filter was designed with a cutoff frequency of 0.1 Hz. This cutoff frequency allowed the filter to remain a 2nd order filter, while removing all unnecessary signals. Priority was given to keeping the filter's order minimal because this algorithm could eventually find its way onto a small 16-bit embedded microcontroller.

The effects of fluid flow introduction and re-building the pressure value by compensating for the pressure drop generated by fluid flow were analyzed.

Bernoulli's principle for an ideal fluid states that the pressure drop due to fluid flow (i.e. kinetic energy per unit volume) can be found by the following relationship:

$$P_{drop} = \frac{1}{2}\rho v^2,$$

where $\rho$ is the density of the fluid, and $v$ is the velocity of the fluid.

Because fluid flow data is available in a network-based cardiopulmonary bypass circuit, we can use this fluid flow data in conjunction with the tubing's inside diameter to predict the velocity of the fluid in the tubing. All experiments were conducted using ⅜" ID (inner diameter) tubing, which results in the following pressure drop function of flow:

$$P_{drop}(\text{Flow}) = 0.110 \text{ Flow}^2 \text{ [inH}_2\text{O]},$$

where flow is in Liters per minute, and the Pressure Drop Coefficient is in inH2O-min2/L2.

To confirm the pressure drop as predicted by Bernoulli, the inlet and outlet of the pump were connected to the reservoir and the pressure sensor was zeroed in the absence of fluid flow. The pump was turned on to introduce fluid flow into the system. Once the system had reached a steady state condition, a pressure measurement was taken. Pressure drop measurements were taken for fluid flow rates from 0 to 6 LPM. The data was fit to a 2nd polynomial in an effort to determine if experiment would match classical theory. To assist the curve-fit, the data was mirrored along the y-axis prior to fitting.

Figure 5:
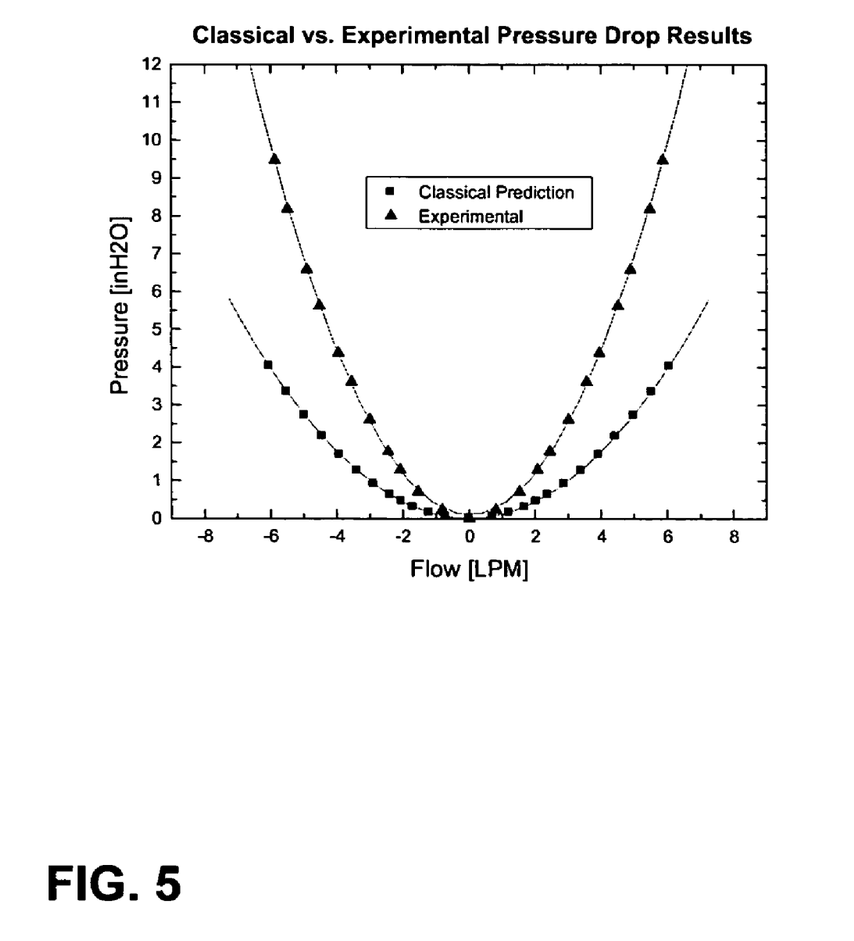

Experimental data fit a 2nd order polynomial very well, with typical standard deviations from the fit in the range of 0.05-0.10. However, the Pressure Drop Coefficient did not match classical theory. FIG. 5 is a graph that displays both expected and experimental results from the pressure drop data.

It was hypothesized that a boundary-layer effect was occurring in the experiment, resulting in little to no flow at the inside walls of the tubing. If this were true, a majority of the flow was occurring in the middle portion of the tubing, resulting in a greater pressure drop than expected.

To test this hypothesis, a 2" ID 6" long section of PVC pipe was inserted inline with the tubing, and a pressure sensor was attached to the side of the PVC pipe. In this case, classical physics predicts uniform flow distribution through the cylinder, reducing the velocity of the fluid such that the pressure drop would be miniscule. Results of this test showed that the 2" ID tubing had almost no effect on the measured pressure drop. This confirmed that fluid flow was occurring in the middle of the tubing, and that the fluid near the perimeter of the tubing was merely acting as a buffer to transfer the pressure signal.

Figure 6:
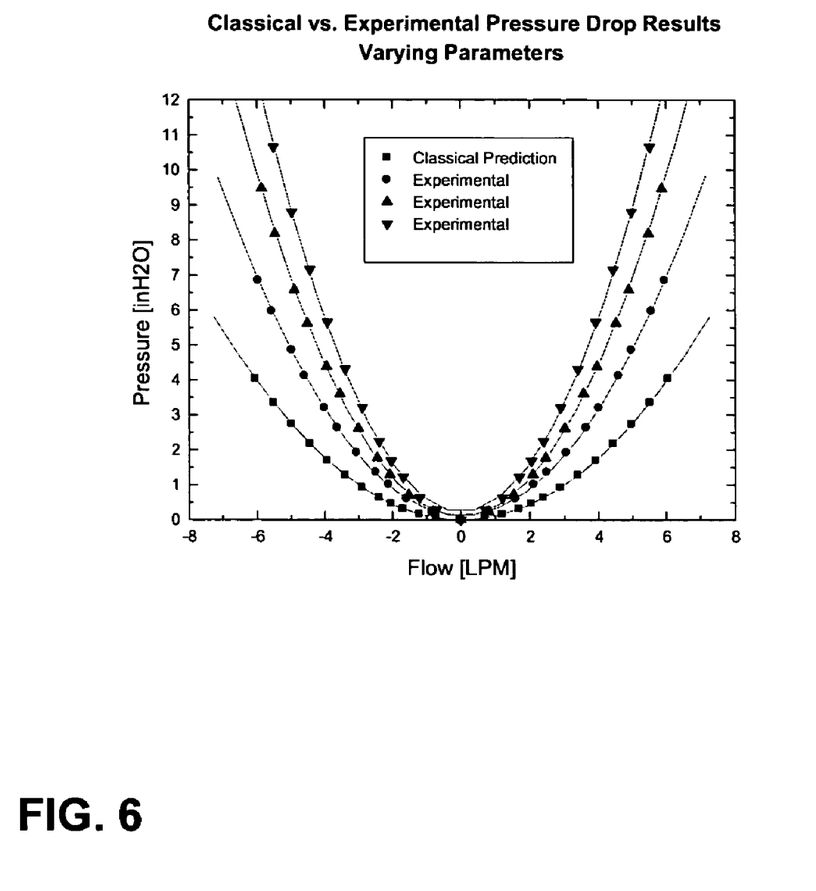

After further experimentation varying parameters such as tubing size, pressure sensor coupler length, pressure sensor attachment mechanism, and distance from the reservoir, it became obvious that the physical configuration of the pressure sensor and the tubing affected the results. In particular, variations in distance from the reservoir seemed to have the greatest effect on the Pressure Drop Coefficient. Varying the aforementioned parameters resulted in Pressure Drop Coefficients from 0.15 to 0.35 in H2O-min2/L2. These results are displayed in FIG. 6.

Fluid Mechanics distinguished two types of flow for a viscous fluid: laminar and turbulent. In distinguishing between the two types of flow, a dimensionless constant called Reynolds's number is introduced. A Reynold's number of less than 2000 implies laminar flow, whereas a number over 4000 implies turbulent flow, and values between 2000 and 4000 represent a transition area. Reynold's number is defined as follows:

$$Re = \rho V D / \mu,$$

where V is fluid velocity, D is pipe diameter, $\rho$ is fluid density, and $\mu$ is fluid viscosity.

For the 3/8" ID tubing used in this test, Reynold's number falls in the laminar region only for fluid flows of less than 1 LPM. Thus, turbulent flow must be considered and applied to this test. Experimentation is the primary means by which turbulent fluid flow characteristics are described, and because turbulence is so complex, its complete analysis and quantification will probably never be achieved.

Figure 7:
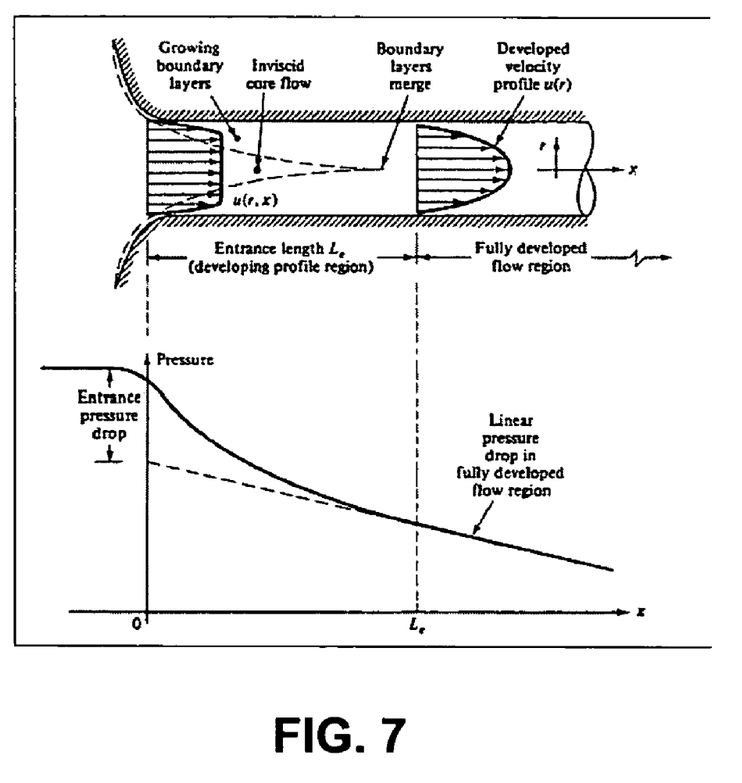

In researching the area of turbulent fluid mechanics, an effect termed the "entrance effect" was encountered. The effect defines a critical distance Le at which fully developed flow occurs at the entrance to a conduit from a reservoir. The effect occurs due to shear where a fluid enters the conduit from a reservoir. FIG. 7 demonstrates this effect.

For turbulent fluid flow, experimentation has shown that the entrance length can be approximated to:

$$L_e/D \sim 4.4 Re^{1/6}.$$

Figure 8:
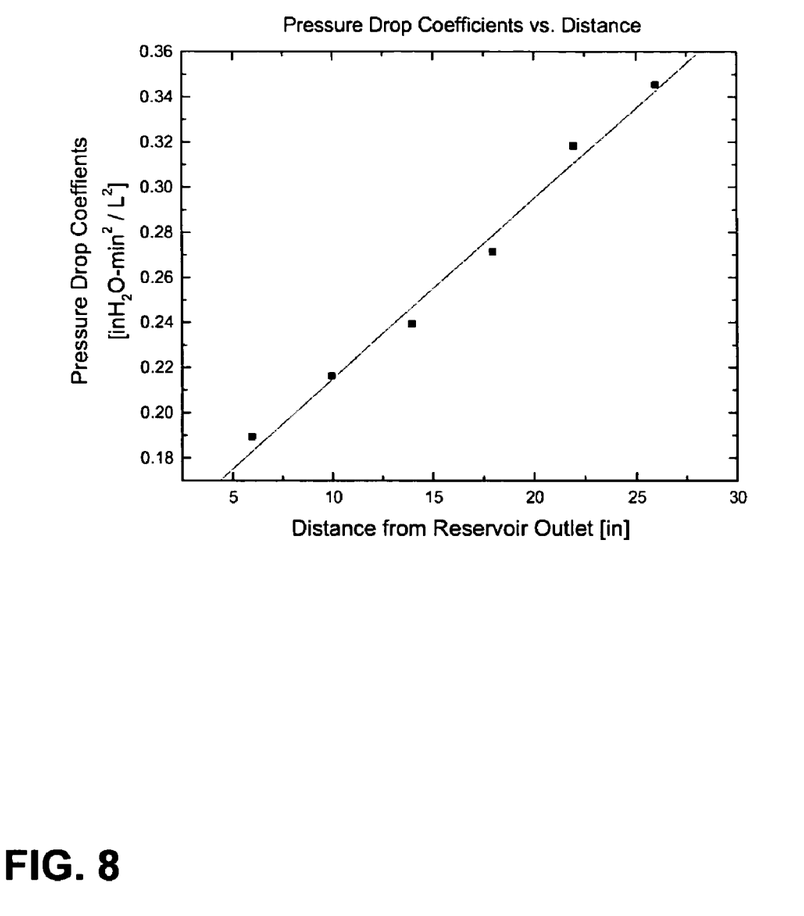

Applying this relationship to the test implies that entrance effects could prevent fully-developed fluid flow for a distance of about 9" from the reservoir outlet. Considering these findings, experiments were conducted that measured the Pressure Drop Coefficient at various distances from the reservoir outlet. Each Pressure Drop Coefficient was determined using pressure/flow data fit to a 2nd order polynomial at distances from 6 to 26 inches from the reservoir outlet in 4" increments. FIG. 8 shows that the Pressure Drop Coefficients increased linearly with distance out to 26 inches.

Because a perfusion circuit will not tolerate the application of a pressure sensor very far from the venous reservoir's outlet, it was not beneficial to pursue entrance effects beyond a distance of 26 inches.

Analysis of pressure drop experimentation revealed that the pressure drop could not be accurately predicted from theory alone. However, if physical conditions are kept constant, the pressure drop responds to various flow rates in a very consistent parabolic fashion. With this data in hand, two recommendations can be made: (1) A preferred physical configuration may be defined and characterized, e.g., a container profile, and (2) a single pressure datapoint can be taken while maintaining constant volume in the reservoir. From this single datapoint, the coefficient of pressure drop can be determined. This datapoint should be taken at a high flow rate so that the Flow$^2$ term is emphasized, and a more accurate Pressure Drop Coefficient can be attained.

In a second test, the 1500 ml Sarns flexible venous reservoir was filled with 750 mL of fluid, and a datapoint was taken at 6 LPM to generate a Pressure Drop Coefficient that would be used throughout the system integration testing. The reservoir was then filled with 1250 ml of fluid, and a centrifugal pump was connected such that it was drawing fluid from the reservoir's outlet, and pumping back into the inlet.

Volume data was generated and gathered at flow rates of 0, 1, 2, 3, 4, 5, and 6 LPM. After each series of data was gathered, 250 ml of fluid were drawn out of the system, and data was gathered again. This was repeated until there were only 250 ml of fluid left in the reservoir. Percentage error between the actual and detected volumes was generated for the various flow and volume conditions, and this data is plotted in FIG. 9.

Figure 9:
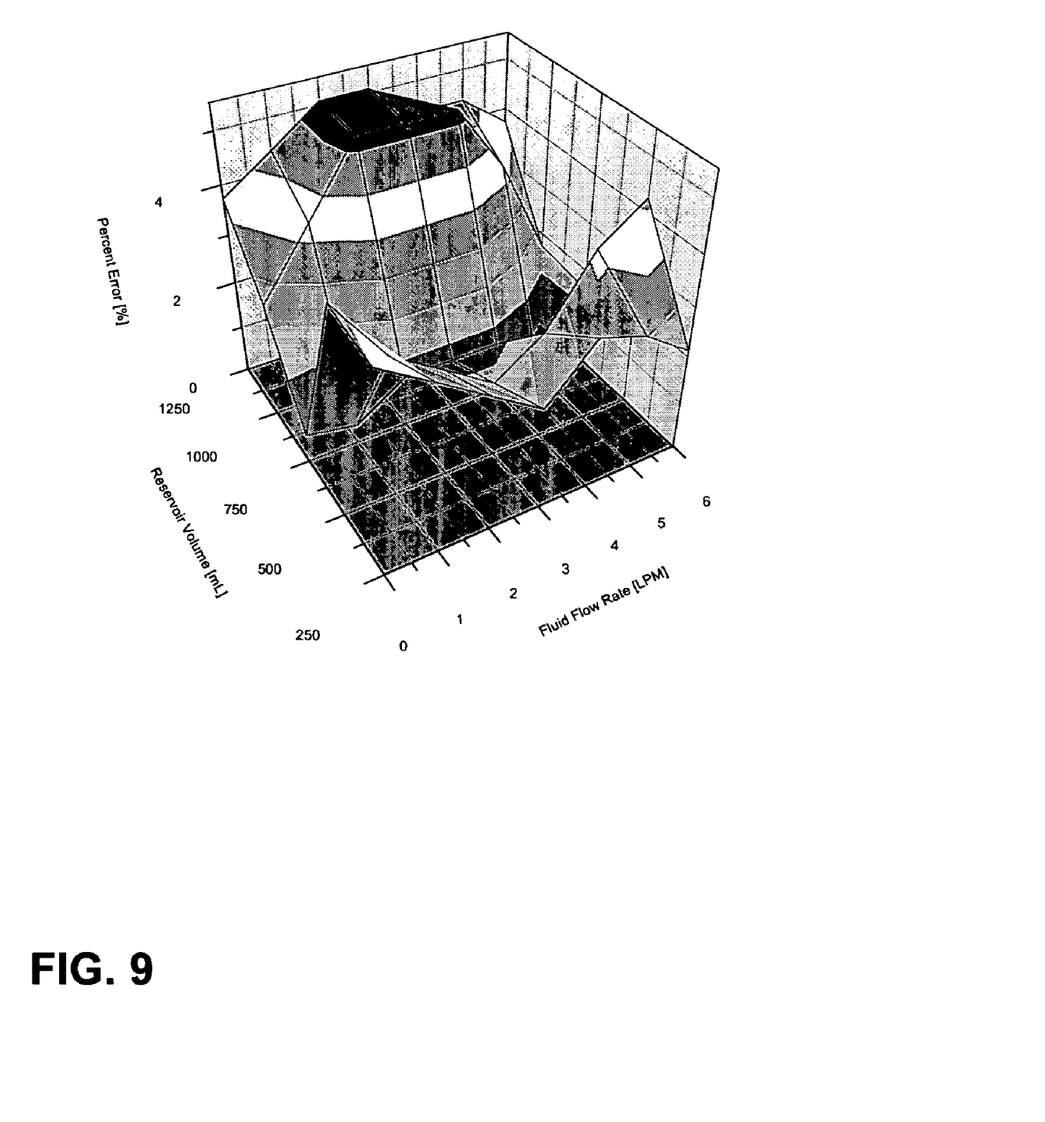

FIG. 9 shows that the system was most accurate at 750 ml. This may be expected for two reasons: (1) this is the most linear region from the Reservoir Pressure-Volume Characterization as seen in FIG. 4; and (2) the pressure drop coefficient was sampled at 750 ml, effectively "tuning" the system for this volume.

Although it was expected that the high flow rates of 5 and 6 LPM would generate more error, they did not. These results demonstrate just how closely the pressure drop curve fit matches the actual pressure drop across various flow rates.

In a third test, a model was developed in which a peristaltic roller pump drives the cardiopulmonary bypass circuit. This pump does not produce a steady flow of fluid;

rather it acts more like a human heart by injecting fluid at spaced intervals. This type of pump adds pressure noise to the system. The pressure sensor not only senses the pressure exerted by the level of the static fluid, it also senses the pressure noise. The output from the pressure will be digitally sampled so it must first pass through an analog anti-alias filter. Because the signal will be sampled at 250 Hz, the low-pass cutoff of the filter was 125 Hz. The signal was then passed to the analog to digital converter and sampled. A 12 bit ADC from National Instruments was used in this test. This digital data was then passed into LabVIEW where it can be processed. In addition, a Hall-Effect device was connected to the rotating shaft of the roller pump. A distinct pulse was generated each time the pump makes a full rotation. This signal was simultaneously passed into LabVIEW where it can also be processed. Finally, the processed information, including the level of the bag and the speed of the pump, was output to a user controlled display panel.

Figure 10:
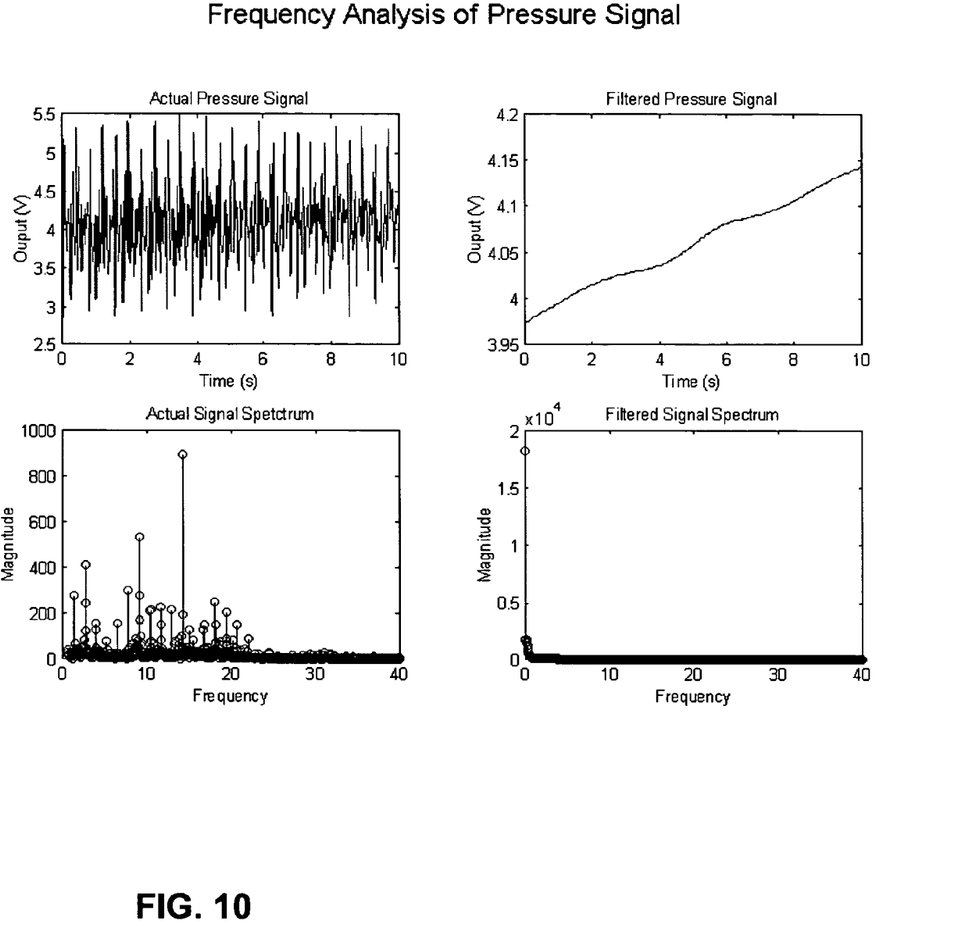

The first part of this test was the removal of the pressure noise added by the roller pump. The upper left corner of FIG. 10 shows the unusable signal with the pressure noise added by the pump. The frequency analysis shown in the bottom left corner of FIG. 10 shows the frequency content of the noise. From this information a filtering scheme was developed. FIG. 10 shows the actual signal and the spectrum before and after low-pass filtering. The filtering was done digitally in real-time with LabVIEW. The cutoff of the Butterworth low-pass was 0.3 Hz with a fourth order response.

As FIG. 10 shows, the system was effective at removing the pressure noise and generating a quiet pressure signal.

Figure 11:
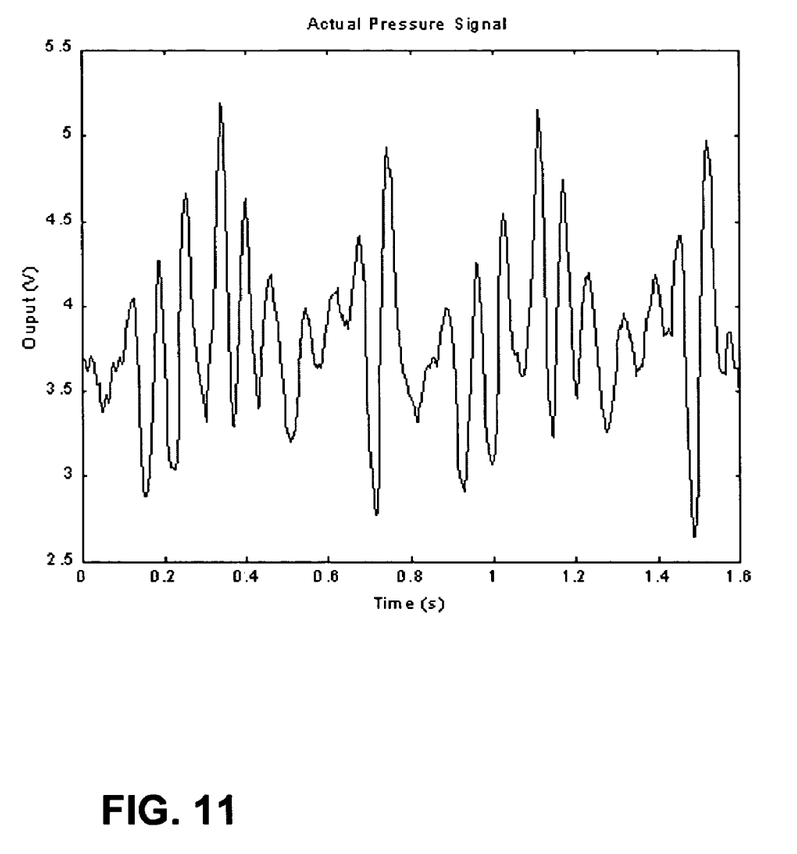

A method was examined for obtaining tachometer information without adding hardware to the system from the original pressure pulses. Each time a roller in the pump passed the tube it would generate a peak in the signal. If the time between these peaks could be determined, the tachometer information would be known. However, in some environments, the pulses may not be consistent enough to generate tachometer information. The wave-shape of four consecutive pressure pulses was shown in FIG. 11.

For this test, Honeywell Series 160 PC Differential Pressure Sensor (0-10" Water) was used. In addition, a low pass analog butterworth filter with cutoff frequency of 125 Hz, a peristaltic roller pump from Cole-Parmer (Drive: EW 07593 Head: EW07019), a hall effect switch (UGN-3013T Hall Effect Digital Switch), and LabVIEW (A/D Fs 250 Hz) display panel were used. The fluid used in this experiment was water as the density of water is similar to that of blood.

Figure 12:
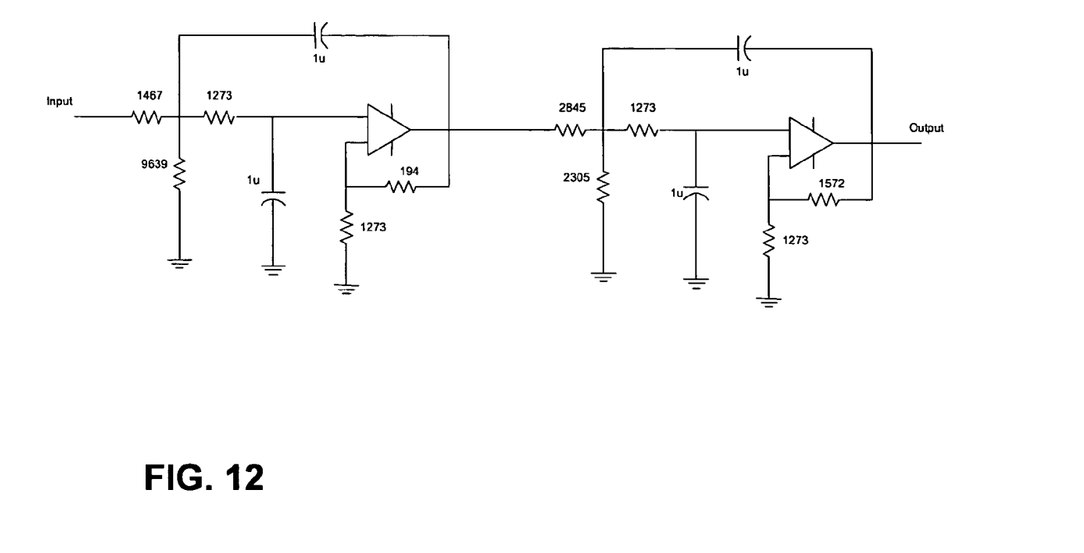
FIG. 12 illustrates a circuit diagram of an active filter for use within the bypass circuit.

FIG. 12 illustrates a circuit diagram of an active filter. This filter has a cutoff frequency of 125 Hz with a third order Butterworth response. The signal is being sampled at 250 Hz, so it may be desirable to keep frequencies of greater than 125 Hz out of the signal. Another filter design would have set the cutoff frequency around 50 Hz. This may have ensured that all frequencies at 125 Hz or higher would have been fully attenuated, not only 3 dB of attenuation as this filter provides. This did not cause any problems for this test because the actual signal did not have any frequency content higher than 45 Hz.

Figure 13:
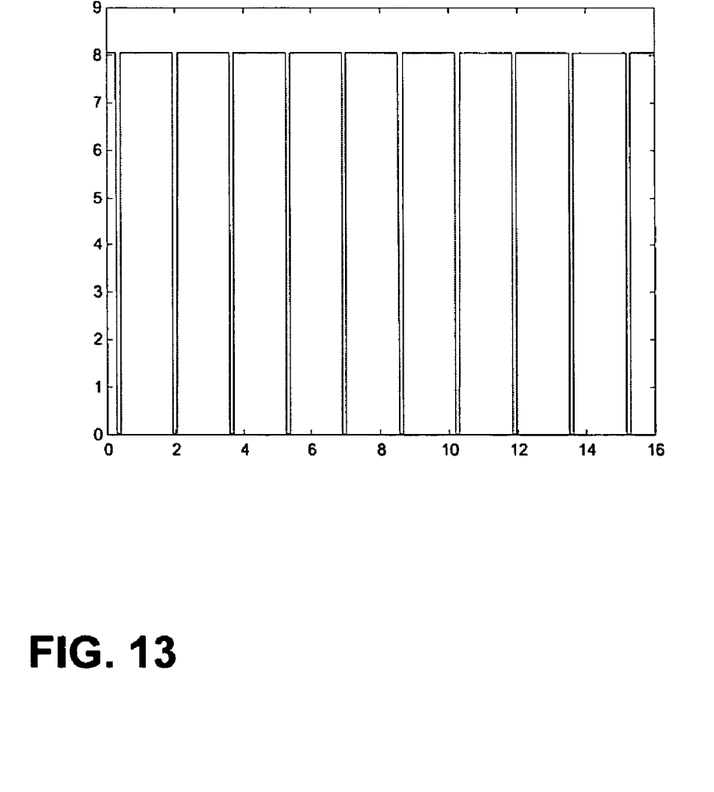
FIG. 13 is a chart illustrating the actual digital pulses used for the timing of the tachometer.

The actual digital pulses used for the timing of the tachometer are shown in FIG. 13. The signal stays high until the magnet on the rotating shaft passes the Hall Effect Device. This method allowed for a consistent and accurate tachometer at the expense of the addition of more hardware and more wires.

Several variations were tested to ensure consistent results. These experiments included: varying the speed of the pump, moving the sensor in relation to the bag, using different size blood bags, and changing the length of the tubing connected to the sensor. None of these variations caused discrepancies.

Various embodiments of the invention have been described. For example, although described in reference to detection of blood within a venous reservoir of a cardiopulmonary bypass circuit, the techniques may be applied to IV pumps, dialysis machines, cardiac assist systems, arthroscopy systems, and the like. These and other embodiments are within the scope of the following claims.

The invention claimed is:

1. A system comprising:
    a venous reservoir for a cardiopulmonary bypass circuit;
    a pressure sensor coupled within the bypass circuit near an outlet of the venous reservoir, wherein the pressure sensor generates a pressure signal representative of a sensed pressure of the bypass circuit;
    a flow sensor coupled within the bypass circuit that generates a flow signal representative of a fluid velocity of the fluid exiting the venous reservoir;
    a controller that computes a volume of blood within the venous reservoir as a function of the pressure signal and the flow signal, and outputs an indicator based on the computed volume; and
    a memory programmed to store a set of container profiles, wherein the controller selects one of the container profiles for the venous reservoir and computes the volume based on the selected profile, and further wherein the container profiles comprise one or more coefficients that are applied by the controller to compute the volume.

2. The system of claim 1, wherein the controller applies a polynomial to map pressure to volume.

3. The system of claim 2, wherein the one or more coefficients of each container profile are associated with a respective type of container, and the controller applies the coefficients of the selected container profile to evaluate the polynomial.

4. The system of claim 1, wherein at least one of the container profiles corresponds to a soft container.

5. The system of claim 1, wherein at least one of the container profiles corresponds to a hard container.

6. The system of claim 1, wherein the controller comprises an input device to receive input from a user for selecting the container profile.

7. The system of claim 1, wherein the controller comprises an input device to receive patient-specific parameters from a user, and wherein the controller computes the volume as a function of the patient-specific parameters.

8. A method comprising:
    generating a set of container profiles, wherein each container profile is associated with a particular type of container that may be used as a venous reservoir, and further wherein the container profiles comprise one or more coefficients;
    storing the set of container profiles within a memory;
    generating a pressure signal representative of a pressure in a cardiopulmonary bypass circuit at a location near an outlet of a venous reservoir;
    selecting one of the container profiles for the venous reservoir;
    computing a volume of blood within the venous reservoir as a function of the pressure signal based on the selected container profile, wherein the coefficients of the selected container profile are applied to compute the volume; and
    outputting an indicator based on the computed volume.

9. The method of claim 8, further comprising generating a flow signal representative of a fluid velocity of the fluid exiting the venous reservoir, wherein computing a volume comprises computing the volume as a function of the flow signal and the pressure signal.

10. The method of claim 8, wherein computing the volume comprises evaluating a polynomial that maps pressure to volume in accordance with the selected container profile.

11. The method of claim 10, wherein the coefficients of each of the container profiles are associated with a respective type of container, and wherein evaluating a polynomial comprises applying the coefficients defined by the selected container profile to evaluate the polynomial.

12. The method of claim 8, wherein at least one of the container profiles corresponds to a soft container.

13. The method of claim 8, wherein at least one of the container profiles corresponds to a hard container.

14. The method of claim 8, further comprising:
receiving input from a user indicating a type of container; and
selecting the container profile based on the input.

15. The method of claim 8, further comprising:
receiving patient-specific parameters from a user; and
computing the volume as a function of the patient-specific parameters.

* * * * *